United States Patent
Voth et al.

(10) Patent No.: US 11,950,833 B1
(45) Date of Patent: Apr. 9, 2024

(54) METHOD AND SYSTEM FOR DETECTING CONTACT STATUS USING ELECTRODE

(71) Applicant: St. Jude Medical, Cardiology Division, Inc., St. Paul, MN (US)

(72) Inventors: Eric J. Voth, Maplewood, MN (US); Jeffrey A. Schweitzer, St. Paul, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 0 days.

(21) Appl. No.: 18/096,188

(22) Filed: Jan. 12, 2023

(51) Int. Cl.
- *A61B 18/12* (2006.01)
- *A61B 5/053* (2021.01)
- *A61B 18/00* (2006.01)

(52) U.S. Cl.
CPC .......... *A61B 18/1206* (2013.01); *A61B 5/053* (2013.01); *A61B 2018/00875* (2013.01)

(58) Field of Classification Search
CPC ................ A61B 18/1206; A61B 5/053; A61B 2018/00875
See application file for complete search history.

(56) References Cited

U.S. PATENT DOCUMENTS

| | | | |
|---|---|---|---|
| 10,188,314 B2 | 1/2019 | Mosesov et al. | |
| 10,398,348 B2 | 9/2019 | Osadchy et al. | |
| 10,750,974 B2 | 8/2020 | Curran | |
| 10,799,148 B2 | 10/2020 | Mosesov et al. | |
| 11,179,194 B2 | 11/2021 | Sliwa et al. | |
| 11,439,319 B2 | 9/2022 | Curran | |
| 11,612,334 B2 | 3/2023 | Mosesov et al. | |
| 11,612,335 B2 | 3/2023 | Mosesov et al. | |
| 2017/0348049 A1* | 12/2017 | Vrba | A61B 18/1492 |
| 2019/0183378 A1* | 6/2019 | Mosesov | A61B 5/068 |
| 2022/0192604 A1 | 6/2022 | Palti et al. | |
| 2023/0077196 A1 | 3/2023 | Curran | |

* cited by examiner

*Primary Examiner* — Michael F Peffley
*Assistant Examiner* — Samantha M Good
(74) *Attorney, Agent, or Firm* — Billion & Armitage

(57) ABSTRACT

A method of determining contact status of electrodes includes applying drive signals between pairs of electrodes, measuring a bipolar electrode complex impedance (BECI) value generated in response to the drive signals over a collection period, and determining a baseline BECI value representing a minimum value measured during the collection period. The method further includes determining contact status of the electrode by applying drive signals between pairs of electrodes over a given interval, measuring a BECI value generated in response to the drive signals, measuring a peak-to-peak value associated with the BECI values measured over the given interval, and determining contact status based on a combination of the baseline BECI value, the measured BECI value, and the peak-to-peak value associated with the measured BECI values.

20 Claims, 7 Drawing Sheets

METHOD AND SYSTEM FOR DETECTING CONTACT STATUS USING ELECTRODE

TECHNICAL FIELD

The present invention relates generally to medical devices and systems and methods of detecting contact between electrodes on the medical device and adjacent tissue based on measured impedances.

BACKGROUND

Catheters are utilized in a number of operations within the human body. In many of these applications, whether collecting data from surrounding tissue or administering treatment, it is important to determine the proximity of the catheter—in particular the electrodes collecting data or administering treatment—with the adjacent tissue. A number of methods are utilized to make this determination, including for example monitoring electrocardiogram signals (e.g., voltage measured between electrodes) and/or impedance of an electrode. For example, impedance is understood, in general, to increase in response to contact with tissue. However, a number of other factors may also result in variations in impedance, including location of the electrode within the body (i.e., different chambers of the heart, exposed to different volumes of blood flow, may exhibit different impedance values) and movement of the surrounding tissue as a result of, for example, heartbeats. These factors make it difficult to rely on raw electrode impedance measurements. It would therefore be beneficial to develop a method of more reliably detecting contact based on such impedance measurements.

SUMMARY

According to some aspects, a method of determining contact status of electrodes includes applying drive signals between pairs of electrodes, measuring a bipolar electrode complex impedance (BECI) value generated in response to the drive signals over a collection period, and determining a baseline BECI value representing a minimum value measured during the collection period. The method further includes determining contact status of the electrode by applying drive signals between pairs of electrodes over a given interval, measuring a BECI value generated in response to the drive signals, measuring a peak-to-peak value associated with the BECI values measured over the given interval, and determining contact status based on a combination of the baseline BECI value, the measured BECI value, and the peak-to-peak value associated with the measured BECI values.

According to another aspect, a system for use with a medical device configured for insertion within a patient includes a signal generator configured to apply a drive signal to one or more pairs of electrodes located on the medical device, a measurement circuit configured to measure responses of the electrode pairs to the drive signal, and a contact assessment module. The contact assessment module is configured to generate bipolar electrode complex impedance (BECI) values for each of the electrode pairs, determine a baseline BECI value representing a minimum BECI value measured during a collection period, subsequently measure a BECI value generated in response to the applied drive signals over a given interval, measure a peak-to-peak value associated with the measured BECI values over the given interval, and determine a contact status based on a combination of the baseline BECI value, the measured BECI value, and the peak-to-peak value associated with the measured BECI values. The system further includes a display for displaying proximities of the electrodes relative to the tissue based on outputs received from the contact assessment module.

According to another aspect, a contact assessment system for determining a contact state of an electrode included as part of an electrode pair located at a distal end of a medical instrument includes an input configured to receive signals collected in response to a source signal applied across the electrode pair and a processor configured to, upon execution of specific program instructions stored on a computer-readable storage medium. Execution of the specific program instructions causes the processor to calculate bipolar electrode complex impedance (BECI) values based on the received input signals during a collection period, determine a baseline BECI value representing a minimum value measured during the collection period, and determine a contact status by subsequently applying drive signals between the electrode pair over a given interval. The processor measures a BECI value generated in response to the applied drive signals over the given interval, measures a peak-to-peak value associated with the measured BECI values over the given interval, and utilizes a combination of the baseline BECI value, the measured BECI value, and the peak-to-peak value associated with the measured BECI values to determine the contact status of the electrode.

DETAILED DESCRIPTION

According to some embodiments, the claimed invention utilizes a bipolar electrode complex impedance (BECI)

measurement to determine proximity or contact status of a pair of electrodes to tissue. The claimed invention utilizes a ratio of a baseline BECI value (representative of the BECI when the electrodes are not in contact with tissue) and a measured BECI value in combination with a peak-to-peak measured BECI value corresponding with a given interval (e.g., one second) to determine contact.

Figure 1:
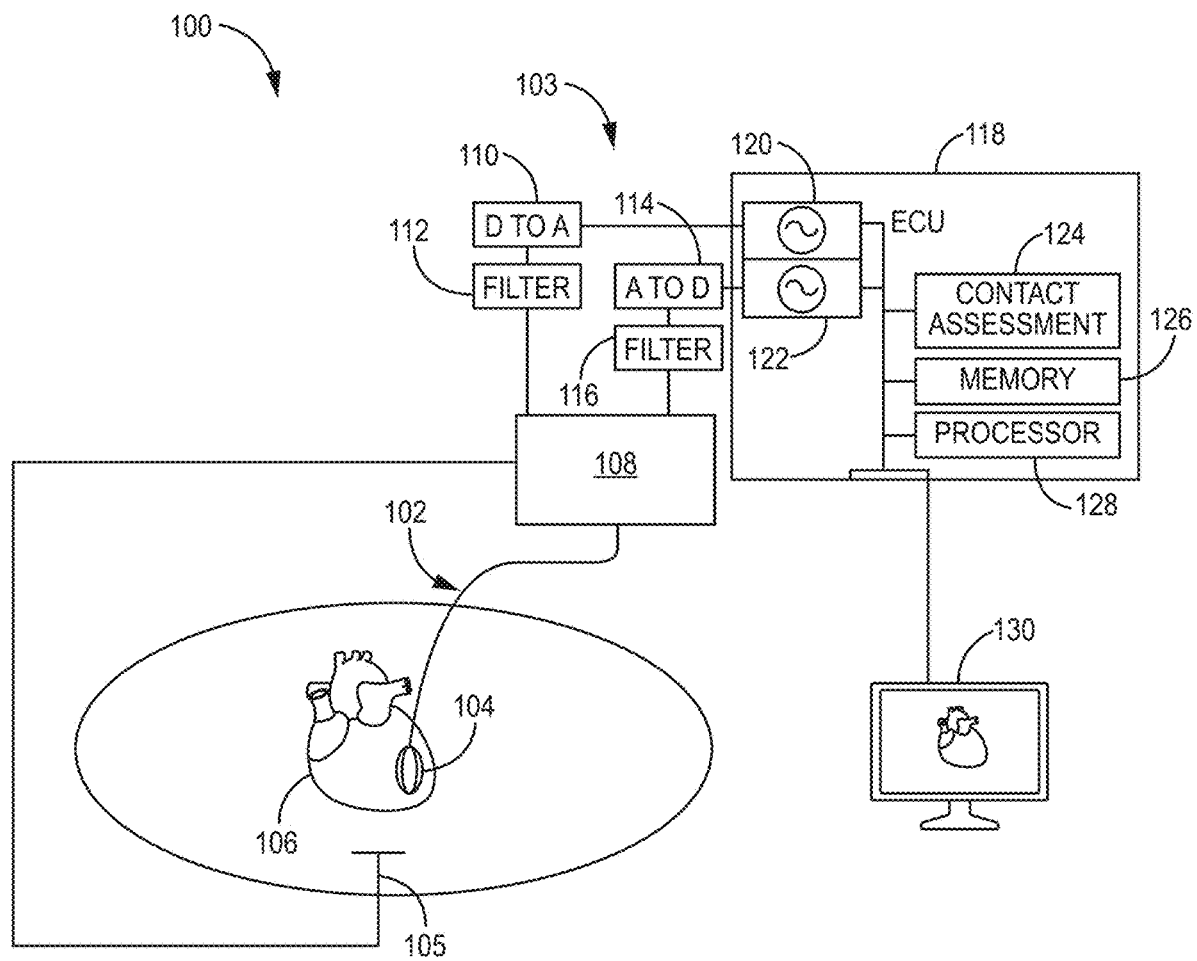
FIG. 1 is a diagrammatic depiction of a system including a medical device for insertion within a patient, the system configured to utilize measured bipolar electrode complex impedances between electrodes to determine proximity or contact status of the one or more electrodes located at a distal end of the medical device according to some embodiments.

FIG. 1 is a diagrammatic depiction of a system 100 including a medical device 102 and a local system 103. In some embodiments, the local system 103 includes a switch 108, a digital-to-analog (D to A) converter 110, a filter 112, an analog-to-digital (A to D) converter 114, a filter 116, a display 130, and an electronic control unit (ECU) 118 that may include a signal source 120, a synchronous demodulator circuit 122, a contact assessment module 124, a memory 126, and a processor 128. In some embodiments, one or more surface patch electrodes 105 may be adhered to the skin of the patient.

In some embodiments, the medical device 102 is an elongate medical device, such as a diagnostic and/or therapy catheter, an introducer, sheath, or other similar type of device. The medical device 102 includes a distal end 104 and a proximal end (not shown) that includes a handle operated by a technician as well as interfaces for interfacing the medical device 102 to the local system 103. The distal end 104 may include various sensors and/or components for localization/navigation of the distal end 104 within the patient, mapping of physiological parameters within the patient, and delivery of therapy. In particular, the distal end 104 of the medical device includes a plurality of electrodes that may be utilized for one or more of these purposes.

Contact status of the one or more electrodes located at the distal end 104 of the medical device 102 is determined based on bipolar electrode complex impedance (BECI) measurements. In general, BECI measurements are generated by driving an excitation signal between two electrodes forming a bipolar pair. The resulting voltage at each of the electrodes is measured and utilized to derive a complex impedance signal. Contact assessment module 124 utilizes the measured BECI measurements to determine contact status as described in more detail with respect to steps shown in FIGS. 3-5. In some embodiments, the term "contact status" is a binary determination, with the electrode either being "in contact" with the tissue or "not in contact" with the tissue. In other embodiments, the term "contact status" may include additional contact states, such as "intermittent contact". In still other embodiments, the term "contact status" may describe a proximity of the electrode to adjacent tissue.

In the embodiment shown in FIG. 1, signal source 120 is utilized to generate the excitation signal. In some embodiments, signal source 120 generates one or more excitation or drive signals each at a unique frequency. More specifically, the signal generator 120 may generate a plurality of excitation or drive signals having unique frequencies within a range from about 1 kHz to over 500 kHz, more typically within a range of about 2 kHz to 200 kHz, and even more typically between about 10 kHz and about 20 kHz, in one embodiment. The drive signals may each have a constant current, typically in the range of between 1-200 µA, and more typically about 5 µA, in one embodiment. The signal generator 120 may also generate signals involved in, for example, determining a location of the electrodes within the body of the patient that may be utilized for mapping, navigation, and/or therapy delivery. The digital signal(s) generated by the signal source 120 are converted to analog signal(s) by D-to-A converter 110 and provided via filter 112 and switch 108 to selected bipolar electrodes. In response to the analog signals supplied between selected bipolar electrodes, a resulting voltage is measured at the electrode pairs by the switch 108, the filter 116, the A-to-D converter 114, a synchronous demodulator circuit 122. In some embodiments, switch 108 selects the electrode to monitor in response to the excitation or drive signal delivered. The filter 116 and the A-to-D converter 114 convert the analog signal to a digital signal that can be operated on by the ECU 118. The synchronous demodulator circuit 122 isolates signals from one another based on the frequency of the excitation or drive signal, allowing a plurality of bipolar electrode pairs to be analyzed approximately simultaneously based on the plurality of excitation or drive signals supplied to the electrode pairs.

In some embodiments, the memory 126 may be configured to store data respective of the medical device 102, the patient, and/or other data (e.g., calibration data). Such data may be known before a medical procedure (medical device specific data, number of catheter electrodes, etc.), or may be determined and stored during a procedure. The memory 126 may also be configured to store instructions that, when executed by the processor 128 and/or a contact assessment module 124, cause the ECU 118 to perform one or more methods, steps, functions, or algorithms described herein. For example, but without limitation, the memory 126 may include data and instructions for determining impedances (e.g., bipolar electrode complex impedance or BECI measurements) respective of one or more electrodes on the medical device 102 and utilizing the impedance measurements to determine a contact status of the one or more electrodes. In some embodiments, the contact assessment module 124 utilizes a processor executing instructions stored on the memory 126, an application specific integrated circuit (ASIC), or other type of processor to execute the functions described in FIGS. 3-5. The ECU may be connected to a display 130, which may display an output of sensed tissue (e.g., heart), the medical device (not shown) and/or determined contact status of the one or more electrodes of the medical device 102.

Figure 2:
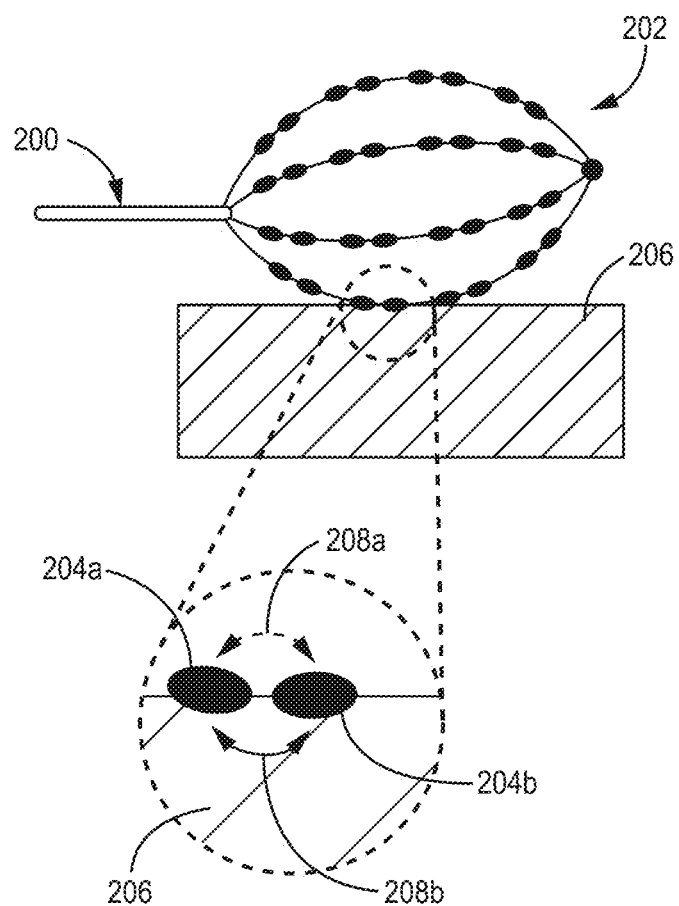
FIG. 2 is a diagrammatic depiction of a distal end of a medical device having a plurality of splines and a plurality of electrodes located on each spline according to some embodiments.

FIG. 2 is a diagrammatic depiction of a distal end 202 of a medical device 200 having a plurality of splines and a plurality of electrodes 204a, 204b located on each spline positioned adjacent cardiac tissue according to some embodiments. In the embodiment shown in FIG. 2, electrodes 204a and 204b form a bipolar electrode pair. A BECI measurement is generated by supplying an excitation signal to electrodes 204a and 204b, resulting in current flowing between the electrodes 204a and 204b as shown by dashed arrows 208a, 208b. The passage of at least a portion of the current 208a, 208b through the patient tissue 206 at the electrode-tissue interface affects the inductive, capacitive, and resistive effects of the electrode response to the drive signal(s). That is, the tissue contact affects the impedance measurements of the electrodes 204a, 204b. In general, if the electrodes 204a, 204b are not in contact with the tissue 206, then the circuit is formed within the blood pool of the patient and the BECI measurement decreases due to the conductive path formed within the blood pool. If the circuit path includes tissue 206 as shown in FIG. 2, then the BECI measurement increases, reflecting the higher impedance of the tissue 206 as compared with measurements taken within the blood pool. As described in more detail with respect to FIGS. 3-5, BECI measurements are utilized to determine tissue contact status of the electrodes. In some embodiments, contact status may include a determination of in contact or not in contact. In other embodiments, contact status may be include other contact status, such as intermittent contact, or a range of contact states.

In other embodiments, the distal end of the medical device may incorporate a plurality of different geometries and/or designs. In some embodiments, the distal end of the medical device is a grid-like array of electrodes shown in more detail in FIG. 7. In other embodiments the distal end of the medical device includes a plurality of splines, but wherein each spline includes only a single electrode as shown in FIG. 8. In this embodiments, bipolar electrode pairs are formed between electrodes located on adjacent splines. In other embodiments, the distal end of the medical device may be curved or loop-like, with a plurality of electrodes spaced along the distal end. Likewise, a variety of different types, geometries, and sizes of electrodes may be utilized at the distal end of the medical device.

Figure 3:
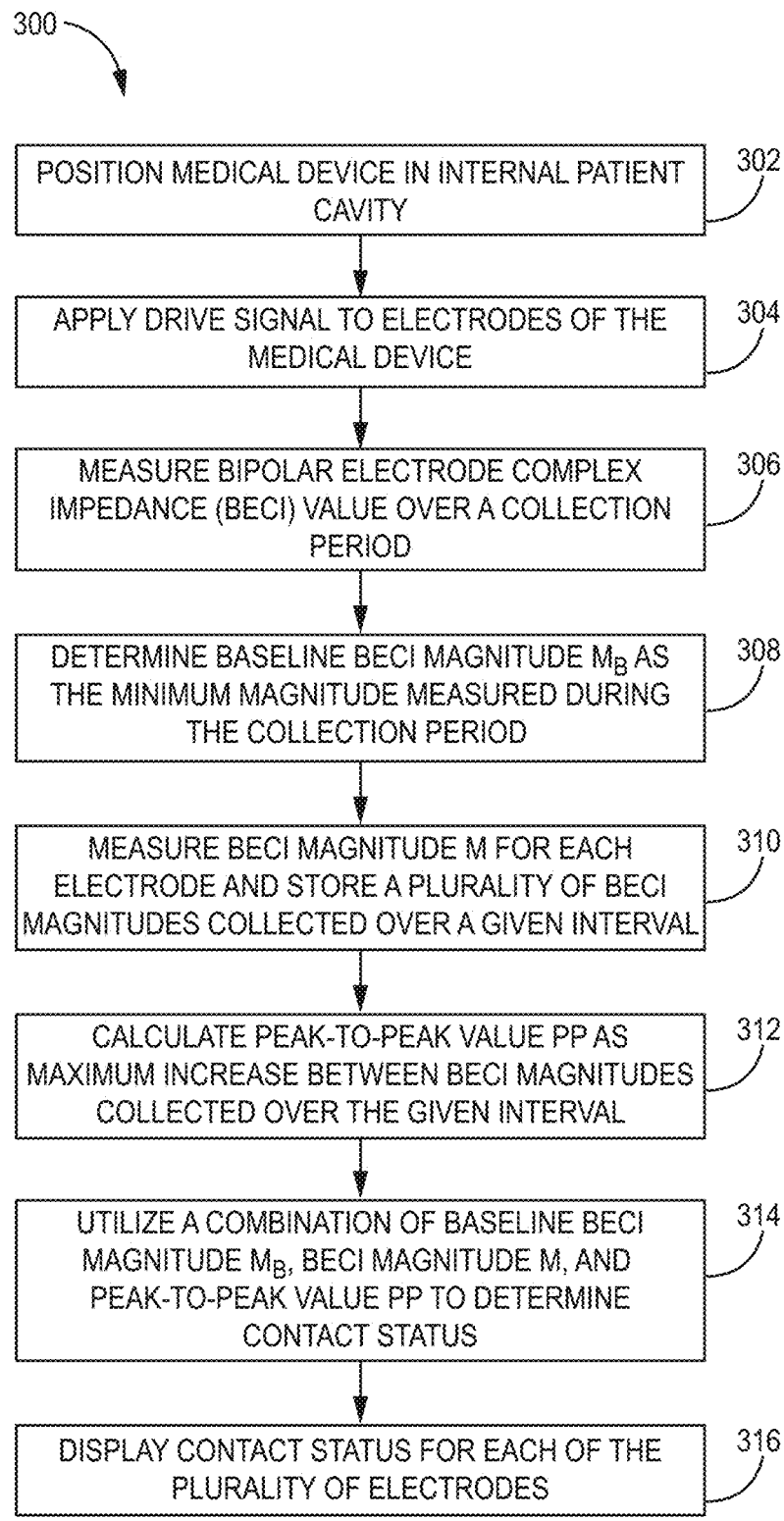
FIG. 3 is a flowchart illustrating steps utilized to determine contact status of electrodes located on a medical device using bipolar electrode complex impedance (BECI) measurements according to some embodiments.

FIG. 3 is a flowchart illustrating steps utilized to determine contact status of electrodes located on a medical device using bipolar electrode complex impedance (BECI) measurements according to some embodiments. BECI measurements include both real and imaginary (quadrature) components. In some embodiments, BECI measurements make use of both the real and imaginary components. In other embodiments, only the real component of BECI measurements are utilized. For the sake of simplicity, reference will be made to BECI measurements that are comprised of only a real component (e.g., magnitude). However, it should be understood that in other embodiments BECI measurements may include both the real and imaginary components. At step 302 the medical device is positioned within an internal patient cavity. For example, in a cardiac application this may include positioning the medical device within the patient's heart or more specifically within one of the chambers of the patient's heart.

At steps 306 and 308, a baseline BECI magnitude is determined for each electrode. Ideally, the baseline BECI magnitude represents the impedance of the electrode when located in the blood pool and not in contact with the tissue. In some embodiments, at step 306, a plurality of BECI measurements are collected for each electrode during a collection period. In general, the lowest BECI measurement recorded during the collection period represents the electrode impedance when the electrode is not in contact with tissue. Thus, at step 308 the baseline BECI value $M_B$ is determined as the minimum magnitude measured during the collection period. As will become evident, one of the benefits of determining a baseline BECI value $M_B$ for each electrode is that differences in impedance resulting from differences in size, geometry, etc. between electrodes are accounted for by determining a baseline BECI value $M_B$ for each individual electrode. For example, with reference to FIG. 2, a baseline BECI value $M_B$ would be determined for electrode 204a and a separate baseline BECI value $M_B$ would be determined for electrode 204b. In some embodiments, the physician may be instructed to move the distal end of the medical device around within the cavity of the patient to ensure a baseline measurement can be established for each electrode in which the electrode is not in contact with tissue.

At step 310, subsequent to determining a baseline BECI value $M_B$ for each electrode, BECI values are measured at one or more of the electrodes. In some embodiments, BECI values are collected over a given interval or window (e.g., one second). In some embodiments, BECI values collected over a given interval or window are stored to memory 126. For example, memory 126 may implement a circular queue in which old measurements are re-written with new measurements. In other embodiments, other data structures may be utilized to collect and store BECI values during a given interval. In some embodiments, the duration of the given interval is equal to approximately one second but may be less than or greater than that depending on the application.

At step 312, the BECI values collected over the given interval are utilized to calculate a peak-to-peak BECI value (PP) that represents the measured difference between a maximum BECI value and a minimum BECI collected for a given electrode within the given interval. In some embodiments, the peak-to-peak BECI value is calculated as an increasing peak-to-peak BECI value, wherein the measured difference is calculated increase in measured BECI values for a given electrode. For a maximum increase peak-to-peak BECI value, if measured BECI values decrease over the given interval, the peak-to-peak BECI value would be zero. Conversely, if the measured BECI values increase over the given interval, the peak-to-peak BECI value would be the difference between the minimum BECI value and the maximum BECI value measured during the interval. As discussed in more detail below, the peak-to-peak BECI value is utilized in combination with the baseline BECI magnitude and a measured BECI magnitude (i.e., most recently measured BECI value) to determine contact status. In some embodiments, a large peak-to-peak BECI value is indicative of (at the very least) intermittent tissue contact for the electrode. In some embodiments, restricting peak-to-peak BECI values to increasing peak-to-peak BECI values is beneficial in preventing a loss of contact with tissue—in which the measured BECI values will likely decrease in response to the electrode moving from contact with the tissue to contact with the blood pool—from being interpreted as tissue contact. That is, it is preferable that if an electrode loses contact with adjacent tissue, the peak-to-peak BECI value does not include the decreasing magnitude of measured BECI values and be interpreted as indicating contact or even intermittent contact with the tissue. Utilizing increasing BECI values to determine the peak-to-peak BECI value ensures that an electrode moving from the blood pool to some level of contact with the adjacent tissue is interpreted as indicating at least some level of contact with the tissue.

At step 314, for each electrode a contact status is determined based on a combination of baseline BECI magnitudes $M_B$, a current BECI magnitude M, and a peak-to-peak BECI value PP over a given interval. Various combinations of these values may be utilized, one of which is described in FIG. 4. In general, the current BECI magnitude M is compared with the baseline BECI magnitude $M_B$—sometimes related to one another as a ratio—as one factor in determining contact status. In addition, the peak-to-peak BECI value provides another factor that can be utilized to determine contact status. By utilizing a combination of the baseline BECI magnitude, current BECI magnitude, and peak-to-peak BECI magnitudes, a more robust determination of contact status is provided based on the bipolar electrode complex impedance measurements.

At step 316, the contact status of each of the plurality of electrodes is displayed to the technician/doctor (e.g., via display 130). In some embodiments, a graphical user interface is provided to display various degrees of contact status (e.g., no contact, intermittent contact, in contact).

Figure 4:
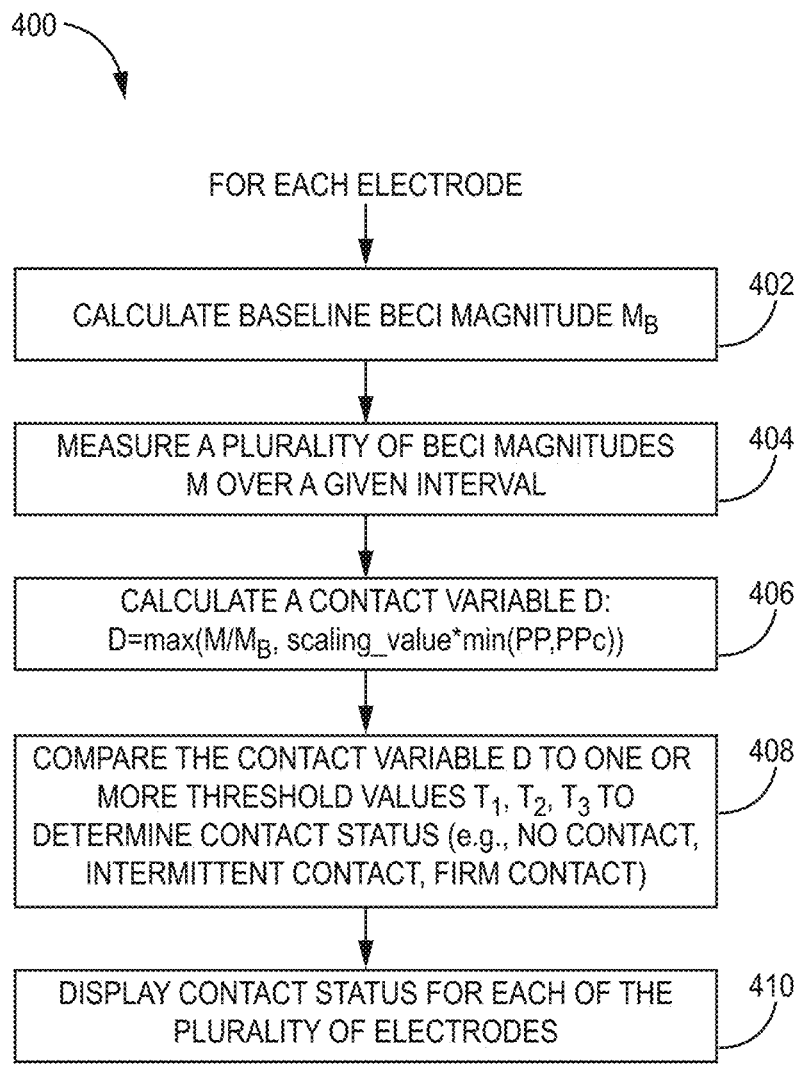
FIG. 4 is a flowchart illustrating steps utilized to determine contact status based on a combination of BECI baseline values, BECI measured values, and peak-to-peak BECI values according to some embodiments.

FIG. 4 is a flowchart illustrating steps utilized to determine contact status based on a combination of BECI baseline values, BECI measured values, and peak-to-peak BECI values to determine a contact variable D according to some embodiments. At step 402, a baseline bipolar impedance complex impedance (BECI) value is calculated for each electrode. As described above, in some embodiments the baseline BECI value for each electrode is determined by monitoring BECI values associated with the electrode over a collection period and selecting the minimum value as the baseline BECI value. In some embodiments, BECI values are filtered so that momentary contact between electrodes resulting in extraordinarily low BECI values are not utilized as baseline BECI values.

At step 404, BECI magnitudes are measured for each electrode over a given interval. As described above with respect to FIG. 3, in some embodiments BECI values collected over a given interval or window are stored to memory 126. For example, memory 126 may implement a circular queue in which old measurements are re-written with new measurements. In other embodiments, other data structures may be utilized to collect and store BECI values during a given interval. In some embodiments, the duration of the given interval is equal to approximately one second but may be less than or greater than that depending on the application.

At step 406, a contact variable D is calculated for each electrode based on a combination of the baseline BECI magnitude, a current BECI measurement, and peak-to-peak BECI measurement. In some embodiments, the peak-to-peak BECI measurement is a difference between a maximum BECI value and a minimum BECI value collected during the given interval. As discussed above, in some embodiments the peak-to-peak BECI measurement is an increasing peak-to-peak BECI measurement, wherein if during a given interval the BECI measurements decline in amplitude then the peak-to-peak BECI measurement would be zero despite a difference between the maximum and minimum BECI value during a given interval.

In the embodiment shown in FIG. 4, the contact variable D is calculated as shown in Equation 1:

$$D = \max\left(\frac{M}{M_B}, S_V * \min(PP, PP_C)\right) \quad \text{Eq. 1}$$

where M is current BECI magnitude measured for a given electrode, $M_B$ is the baseline BECI value calculated for the given electrodes, PP is the peak-to-peak BECI measurement calculated during the given interval, $PP_C$ is a ceiling or maximum peak-to-peak BECI measurement, and the $S_V$ is a scaling variable selected to properly scale the peak-to-peak BECI measurements to the reference frame of the ratio defined by $M/M_B$. In this embodiment, the term $M/M_B$ is referred to as a ratio value and if the baseline BECI magnitude $M_B$ is properly selected should be approximately equal to '1' when the electrode is not in contact with tissue and should increase in magnitude as the electrode is brought into contact with the tissue and the current BECI measurement increases. Likewise, the peak-to-peak BECI measurement PP is zero if there is no change (or only a negative deflection) in the BECI measurements taken during a given interval and increases up to a maximum value defined by the ceiling peak-to-peak value $PP_C$. The peak-to-peak value BECI measurement increases in response to the electrode moving from the blood pool into contact with tissue. In this embodiment, the contact variable D is set equal to the maximum between the term $$\frac{M}{M_B} \text{ and } S_V * \min(PP, PP_C).$$

In some embodiments, the scaling variable $S_V$ is set equal to $(T_1-1.0)/PP_b$, wherein $T_1$ is the threshold utilized to indicate contact with tissue and $PP_b$ is the base peak-to-peak value that would indicate at least intermittent contact (i.e., any peak-to-peak value PP greater than $PP_b$ would indicate at least intermittent contact).

At step 408 the contact variable D is compared to one or more threshold values to determine contact status of each of the plurality of electrodes. In some embodiments, only a single threshold value is required. If the contact variable D is less than the threshold value then the electrode is assigned a 'no contact' status. If the contact variable D is greater than the threshold value then the electrode is assigned an 'in contact' status. In general, the threshold value is greater than '1' and may vary based on the type of device (or type of electrode) being analyzed. In other embodiments, a plurality of thresholds may be utilized, wherein each threshold indicates a different level of contact. For example, in some embodiments, if the contact variable D is less than a first threshold $T_1$, a 'no contact' status is assigned to the electrode. If the contact variable D is greater than the first threshold an 'intermittent contact' status is assigned to the electrode, and if the contact variable D is greater than a second threshold $T_2$ an 'in contact' status is assigned to the electrode. In other embodiments, additional thresholds may be utilized to further delineate various stages of contact between the electrode and tissue.

At step 410, the contact status is displayed for each of the plurality of electrodes. In some embodiments, display may include coloring the electrodes based on the assigned contact status. In other embodiments, various other means of indicating the contact status of each electrode may be utilized. In some embodiments, the contact status is displayed as a running average of contact variable D over a given number of samples. For example, in some embodiments the contact variable D is averaged over 25 samples (e.g., one second) to smooth out sudden variations in the contact variable D. In some embodiments, the number of samples utilized to average the contact variable can be modified. For example, decreasing the number of samples would increase the responsiveness of the contact variable (at the cost of more jitter in the contact variable), while increasing the number of samples would provide a more stable contact assessment but at a cost of slower responsiveness to changes in contact status.

Figure 5:
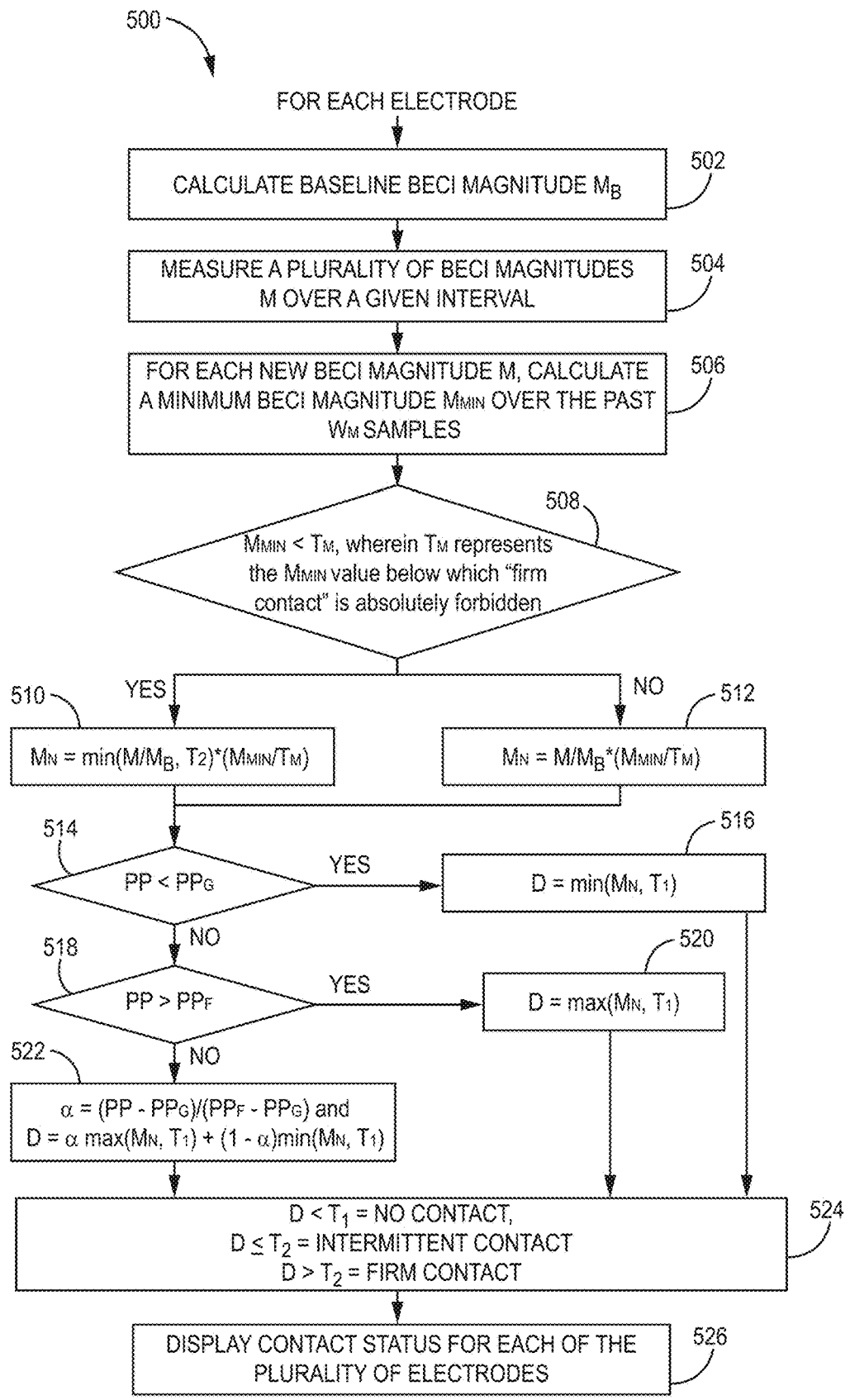
FIG. 5 is a flowchart illustrating steps utilized to determine contact status based on a combination of BECI baseline values, BECI measured values, and peak-to-peak BECI values according to some embodiments.

FIG. 5 is a flowchart illustrating steps utilized to determine contact status based on a combination of BECI baseline values, BECI measured values, and peak-to-peak BECI values according to another embodiment. At step 502, a baseline bipolar impedance complex impedance (BECI) value is calculated for each electrode. As described above, in some embodiments the baseline BECI value for each electrode is determined by monitoring BECI values associated with the electrode over a collection period and selecting the minimum value as the baseline BECI value. In some embodiments, BECI values are filtered so that momentary contact between electrodes resulting in extraordinarily low BECI values are not utilized as baseline BECI values.

At step 504, BECI magnitudes are measured for each electrode over a given interval. As described above with respect to FIGS. 3 and 4, in some embodiments BECI values collected over a given interval or window are stored to memory 126. For example, memory 126 may implement a circular queue in which old measurements are re-written with new measurements. In other embodiments, other data structures may be utilized to collect and store BECI values during a given interval. In some embodiments, the duration of the given interval is equal to approximately one second but may be less than or greater than that depending on the application.

At step 506, for each new BECI magnitude M measured, a minimum BECI value $M_{min}$ is selected from the past $W_M$ samples. In some embodiments, the number of sample $W_M$ corresponds with the length of the given interval. In other embodiments, the number of sample $W_M$ is independent of the given interval.

At step 508, the minimum BECI value $M_{min}$ is compared to a threshold value $T_M$, wherein $T_M$ represents the $M_{min}$ value below which "firm contact" is absolutely forbidden. As a result, the comparison at step 508 determines whether a measured BECI value within the past $W_M$ samples was assigned a value that would indicate the electrode was not in "firm contact" with tissue during the past $W_M$ samples. If the minimum BECI value $M_{min}$ is less than the threshold value $T_M$, then at step 510 a BECI value $M_N$ is calculated based on the following equation:

$$M_N = \min\left(\frac{M}{M_B}, T_2\right) * \left(\frac{M_{min}}{T_M}\right) \qquad \text{Eq. 2}$$

where M is the current BECI measurement, $M_B$ is the baseline BECI measurement, $T_2$ is the threshold compared to the contact variable D, above which "firm contact" is assigned, $M_{min}$ is the minimum BECI measurement selected from the past $W_M$ samples, and $T_M$ is the $M_{min}$ value below which "firm contact" is forbidden. In this way, the minimum is selected between the ratio value ($M/M_B$) and the threshold value $T_2$, and the resulting minimum is multiplied by the term $$\frac{M_{min}}{T_M},$$

which be definition must be less than 1 and therefore reduces the selected minimum between the respective terms $$\frac{M}{M_b} \text{ and } T_2.$$

This selection at step 510—based on the minimum BECI magnitude $M_{min}$ indicating at least recent intermittent contact—prevents the current BECI magnitude M from dominating the calculation of $M_N$ to a value greater than the second threshold $T_2$ (wherein contact value D greater than the second threshold $T_2$ indicates "firm contact"). Conversely, if the minimum BECI value $M_{min}$ is greater than the threshold value $T_M$ at step 508, then at step 512 the BECI value $M_N$ is calculated based on the following equation:

$$M_N = M/M_b * \left(\frac{M_{min}}{T_M}\right) \qquad \text{Eq. 3}$$

In contrast with Equation 2 selected if the $M_{MIN} < T_M$, Equation 3 does not select the minimum between the ratio value $M/M_B$ and the threshold $T_2$. Because the term $M_{min}$ did not indicate intermittent contact within the past $W_M$ cycles, the ratio value is $M/M_B$ is not restricted to a ceiling defined by the threshold $T_2$ and may therefore be assigned a higher value based on the greater likelihood that the electrode is in contact with tissue. In this way, the embodiment shown in FIG. 5 utilizes the minimum BECI value $M_{min}$ to modify the BECI value $M_N$, in particular by setting a ceiling on the maximum value of the BECI value $M_N$ if the minimum BECI value $M_{min}$ indicates that firm contact is not possible. Having defined the BECI value $M_N$ based on the minimum BECI value $M_{min}$ measured in the last $W_M$ cycles and the ratio value defined by M/Ma at steps 510 or 512, at steps 514, 518, and 522 the peak-to-peak BECI value PP is compared to various thresholds to select the contact value D.

At step 514, the peak-to-peak BECI value PP is compared to the threshold value $PP_G$, wherein $PP_G$ is the peak-to-peak value below which "no contact' is an absolute certainty. If the measured peak-to-peak BECI value PP is less than the threshold value $PP_G$, indicating that the measured peak-to-peak BECI value does not indicate any contact, then at step 516 the contact value D is set equal to the minimum of the $M_N$ and the threshold $T_1$. In this way, if the peak-to-peak value PP indicates contact is unlikely, then the contact value D is assigned a ceiling defined by the threshold $T_1$, wherein a contact value D below $T_1$ indicates no contact.

If the peak-to-peak value PP is greater than $PP_G$, then at step 518 the peak-to-peak value PP is compared to the threshold value $PP_F$, wherein the threshold value $PP_F$ is the PP value above which "no contact" is absolutely forbidden or impossible (that is, the peak-to-peak value that indicates at least intermittent contact with tissue). If the peak-to-peak value PP is greater than the threshold value $PP_F$, then at step 520 the contact value D is assigned the maximum of the BECI value $M_N$ and the threshold value $T_1$. In this way, if the peak-to-peak value PP indicates at least some contact is likely, then the contact value D is constrained by a floor defined by the threshold $T_1$ (that is, the contact value D cannot be assigned a value lower than the threshold value $T_1$), wherein a contact value D of at least $T_1$ indicates at least some intermittent contact.

If the peak-to-peak value PP is greater than the threshold $PP_G$ at step 514, but less than the threshold value $PP_F$ a step 518, indicating that the peak-to-peak value PP does not indicate certain no contact or certain contact, then at step 522 the contact value D is assigned a value based on the equation:

$$D = \alpha \max(M_N, T_1) + (1-\alpha)\min(M_N, T_1) \qquad \text{Eq. 4}$$

wherein $$\alpha = (PP - PP_G)/(PP_F - PP_G) \qquad \text{Eq. 5}$$

In this way, the term α represents a magnitude of the peak-to-peak BECI with respect to the thresholds $PP_G$ and $PP_F$. For example, if the peak-to-peak value PP is approximately equal to the upper PP threshold $PP_F$, then the value of a approaches '1' and increases the impact of the term '$\max(M_N, T_1)$' while decreasing the impact of the second term '$\min(M_N, T_1)$'. Conversely, if the peak-to-peak value PP is approximately equal to the lower PP threshold $PP_G$, then the value of a will approach '0' and will increase the impact of the second term '$\min(M_N, T_1)$' while decreasing the impact of the first term '$\max(M_N, T_1)$'.

At step 524, the contact value D is compared to the thresholds $T_1$ and $T_2$ to determine the contact status (e.g., $D<T_1$=no contact, $D≤T_2$=intermittent contact, and $D>T_2$=firm contact).

At step 526 the contact status is displayed for each of the plurality of electrodes. As discussed above, in some embodiments, display may include coloring the electrodes based on the assigned contact status. In other embodiments, various other means of indicating the contact status of each electrode may be utilized. In some embodiments, the contact status is displayed as a running average of contact variable D over a given number of samples. For example, in some embodiments the contact variable D is averaged over samples (e.g., one second) to smooth out sudden variations in the contact variable D. In some embodiments, the number of samples utilized to average the contact variable can be modified. For example, decreasing the number of samples would increase the responsiveness of the contact variable (at the cost of more jitter in the contact variable), while increasing the number of samples would provide a more stable contact assessment but at a cost of slower responsiveness to changes in contact status.

Figure 6:
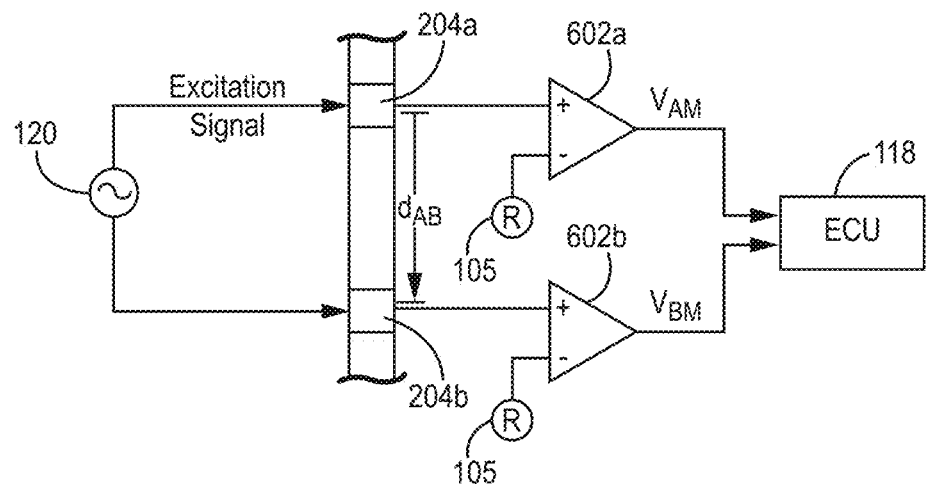
FIG. 6 is a diagrammatic view of components utilized to measure impedance between two electrodes located on the medical device according to some embodiments.

FIG. 6 is a circuit diagram illustrating the circuit elements utilized to excite the bipolar pair of electrodes and measure the resulting complex impedance according to some embodiments. In particular, the circuit diagram includes a signal source 120 (shown in FIG. 1), a pair of electrodes 204a, 204b (shown in FIG. 2), first and second operational amplifiers 602a, 602b, and ECU 118 (also shown in FIG. 1). In some embodiments, the signal source 120 generates an excitation signal that is provided to first and second electrodes 204a, 204b. The first op-amp 602a includes a first terminal (e.g., positive terminal) connected to the first electrode 204a and a second terminal (e.g., negative terminal) connected to a reference electrode 105 (e.g., surface electrode). The output of the op-amp 602a reflects the difference in voltage between the first electrode 204a and the reference electrode 105. The second op-amp 602b includes a first terminal (e.g., positive terminal) connected to the second electrode 204b and a second terminal (e.g., negative terminal) connected to a reference electrode 105 (e.g., surface electrode). The output of the op-amp 602b reflects the difference in voltage between the second electrode 204b and the reference electrode 105. The respective outputs of the first op-amp 602a and the second op-amp 602b are provided to the ECU 118, which utilizes the respective measurements to determine the bipolar electrode complex impedance (BECI).

Figure 7:
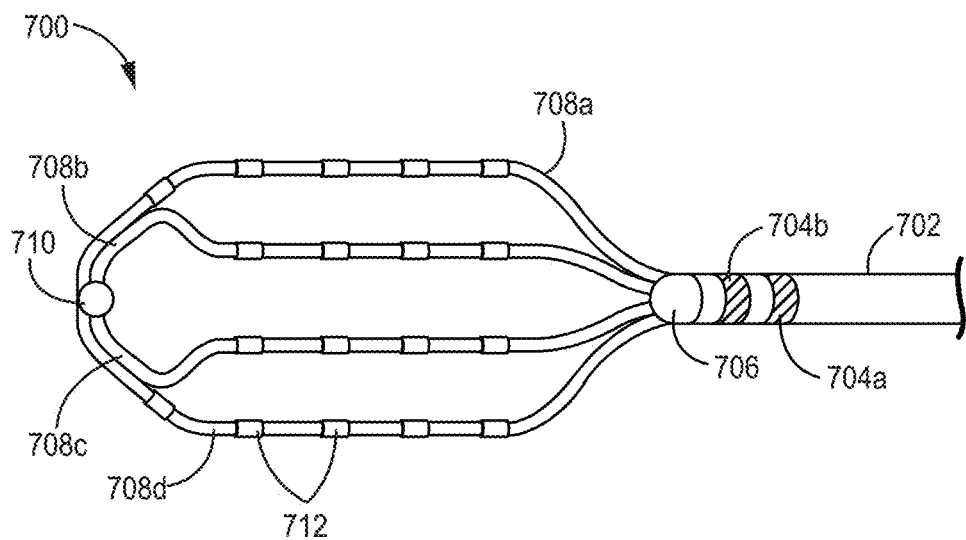
FIG. 7 is a diagrammatic depiction of a distal end of a medical device having an array of electrodes positioned in a plane according to some embodiments.
Figure 8:
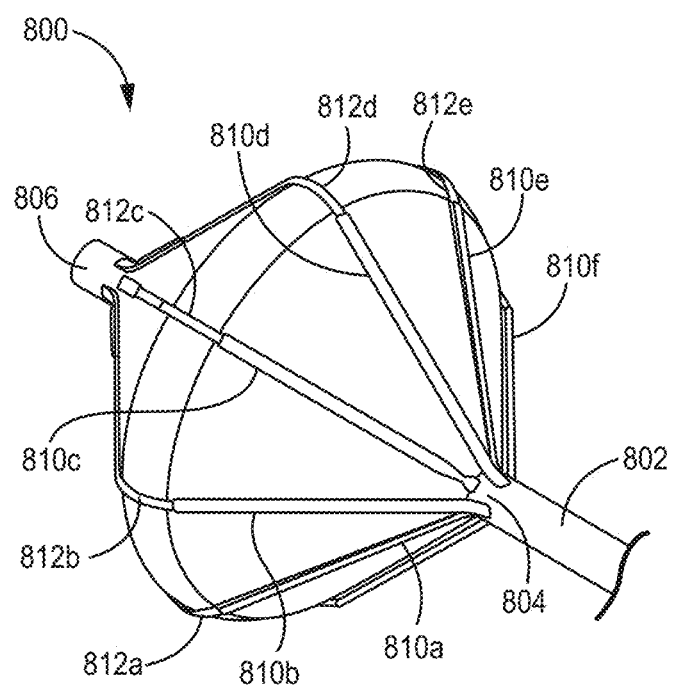
FIG. 8 is a diagrammatic depiction of a distal end of a medical device having a plurality splines for carrying one or more electrodes according to some embodiments.

FIG. 7 is top view of a grid array catheter 700. In some embodiments, grid array catheter 700 includes a shaft 702, shaft electrodes 704a and 704b, a proximal end 706, a plurality of splines 708a, 708b, 708c, 708d, a distal end 710, and a plurality of spline electrodes 712. In some embodiments, bipolar electrode complex impedance measurements may be taken between any pair of adjacent electrodes. For example, a BECI measurement may be taken between shaft electrodes 704a, 704b. In other embodiments, a BECI measurement may be taken between any pair of spline electrodes 712 and the methods described with respect to FIGS. 3-5 may be utilized to assess a contact state or proximity of the plurality of electrodes 704, 712 to adjacent tissue.

FIG. 8 is an isometric view of a basket catheter 800. In some embodiments, basket catheter 800 includes a shaft 802, a proximal end 804, a distal end 806, and a plurality of splines 810a-810f extending between the proximal end 804 and the distal end 806. Each of the plurality of splines 810a-810f includes a corresponding electrode 812a-812f. In some embodiments, BECI measurements may be taken between pairs of adjacent electrodes such as between electrode 812a and 812b, or between electrodes 812c and 812d and the methods described with respect to FIGS. 3-5 may be utilized to assess a contact status or proximity of each of the electrodes to adjacent tissue.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

Discussion of Possible Embodiments

The following are non-exclusive descriptions of possible embodiments of the present invention.

According to some aspects, a method of determining contact status of electrodes includes applying drive signals between pairs of electrodes, measuring a bipolar electrode complex impedance (BECI) value generated in response to the drive signals over a collection period, and determining a baseline BECI value representing a minimum value measured during the collection period. The method further includes determining contact status of the electrode by applying drive signals between pairs of electrodes over a given interval, measuring a BECI value generated in response to the drive signals, measuring a peak-to-peak value associated with the BECI values measured over the given interval, and determining contact status based on a combination of the baseline BECI value, the measured BECI value, and the peak-to-peak value associated with the measured BECI values.

The method of the preceding paragraph can optionally include, additionally and/or alternatively any, one or more of the following features, steps, configurations and/or additional components.

For example, the BECI value may include a real component and a quadrature component, wherein the baseline BECI value, the measured BECI value, and the peak-to-peak value all represent magnitudes of the BECI value.

The step of determining a baseline BECI value representing a minimum value measured during the collection period may include applying a filter to the measured BECI values to filter erroneous minimum values resulting from contact with other electrodes.

The step of measuring a peak-to-peak value associated with the measured BECI values over the given interval may include calculating a largest positive deflection in BECI values measured over the given interval.

The step of determining contact status based on a combination of the baseline BECI value, measured BECI value, and peak-to-peak value may further include calculating a ratio value that represents the ratio of the measured BECI value to the baseline BECI value, scaling at least one of the ratio value or the peak-to-peak value to allow comparison of the ratio value to the peak-to-peak value, defining a variable as a maximum of the ratio value and the peak-to-peak value scaled accordingly, and comparing the variable to one or more threshold values to determine a contact status.

The step of determining contact status based on a combination of the baseline BECI value, the measured BECI value, and the peak-to-peak value may further include applying an equation:

$$D = \max\left(\frac{M}{M_B},\ S_V * \min(PP, PP_C)\right),$$

where D is a contact variable, M is the measured BECI value, $M_B$ is the baseline BECI value, PP is the peak-to-peak value calculated during the given interval, $PP_C$ is a ceiling or maximum peak-to-peak BECI measurement, and $S_V$ is a scaling variable selected to properly scale the peak-to-peak BECI measurements to a reference frame of a ratio defined by $M/M_B$.

The method may further include comparing the contact variable to one or more threshold values to determine the contact status, wherein if the contact variable is less than a first threshold then a 'no contact' status is assigned, greater than a first threshold and less than a second threshold an 'intermittent contact' status is assigned, and greater than the second threshold a 'good contact' status is assigned.

According to another aspect, a system for use with a medical device configured for insertion within a patient includes a signal generator configured to apply a drive signal to one or more pairs of electrodes located on the medical device, a measurement circuit configured to measure responses of the electrode pairs to the drive signal, and a contact assessment module. The contact assessment module is configured to generate bipolar electrode complex impedance (BECI) values for each of the electrode pairs, determine a baseline BECI value representing a minimum BECI value measured during a collection period, subsequently measure a BECI value generated in response to the applied drive signals over a given interval, measure a peak-to-peak value associated with the measured BECI values over the given interval, and determine a contact status based on a combination of the baseline BECI value, the measured BECI value, and the peak-to-peak value associated with the measured BECI values. The system further includes a display for displaying proximities of the electrodes relative to the tissue based on outputs received from the contact assessment module.

The system of the preceding paragraph can optionally include, additionally and/or alternatively any, one or more of the following features, configurations and/or additional components.

For example, the contact assessment module may determine a baseline BECI value representing a minimum value measured during the collection period by applying a filter to the measured BECI values to filter erroneous minimum values resulting from contact with other electrodes.

The contact assessment module may measure a peak-to-peak value by calculating a largest positive deflection in BECI values measured over the given interval.

The contact assessment module may determine contact status based on a combination of the baseline BECI value, measured BECI value, and peak-to-peak value by calculating a ratio value that represents the ratio of the measured BECI value to the baseline BECI value, scaling at least one of the ratio value or the peak-to-peak BECI value to allow comparison of the ratio value to the peak-to-peak BECI value, defining a variable as a maximum of the ratio value and the peak-to-peak value scaled accordingly, and comparing the variable to one or more threshold values to determine a contact status.

The contact assessment module may determine contact status based on the formula:

$$D = \max\left(\frac{M}{M_B},\ S_V * \min(PP, PP_C)\right),$$

where D is a contact variable, M is the measured BECI value, $M_B$ is the baseline BECI value, PP is the peak-to-peak value calculated during the given interval, $PP_C$ is a ceiling or maximum peak-to-peak BECI measurement, and $S_V$ is a scaling variable selected to properly scale the peak-to-peak BECI measurements to a reference frame of a ratio defined by $M/M_B$.

The contact assessment module may compare the contact variable D to one or more threshold values to determine the contact status, wherein if the contact variable is less than a first threshold then a 'no contact' status is assigned, greater than a first threshold and less than a second threshold an 'intermittent contact' status is assigned, and greater than the second threshold a 'good contact' status is assigned.

According to another aspect, a contact assessment system for determining a contact state of an electrode included as part of an electrode pair located at a distal end of a medical instrument includes an input configured to receive signals collected in response to a source signal applied across the electrode pair and a processor configured to, upon execution of specific program instructions stored on a computer-readable storage medium. Execution of the specific program instructions causes the processor to calculate bipolar electrode complex impedance (BECI) values based on the received input signals during a collection period, determine a baseline BECI value representing a minimum value measured during the collection period, and determine a contact status by subsequently applying drive signals between the electrode pair over a given interval. The processor measures a BECI value generated in response to the applied drive signals over the given interval, measures a peak-to-peak value associated with the measured BECI values over the given interval, and utilizes a combination of the baseline BECI value, the measured BECI value, and the peak-to-peak value associated with the measured BECI values to determine the contact status of the electrode.

The contact assessment system of the preceding paragraph can optionally include, additionally and/or alternatively any, one or more of the following features, configurations and/or additional components.

For example, the processor may output the determined contact status to a display.

The step of determining a baseline BECI value representing a minimum value measured during the collection period may further include applying a filter to the measured BECI values to filter erroneous minimum values resulting from contact with other electrodes.

The step of measuring a peak-to-peak BECI value associated with the measured BECI values over the given interval may further include calculating a largest positive deflection in BECI values measured over the given interval.

The step of determining contact status based on a combination of the baseline BECI value, measured BECI value, and peak-to-peak value may further include calculating a ratio value that represents the ratio of the measured BECI value to the baseline BECI value, scaling at least one of the ratio value or the peak-to-peak BECI value to allow comparison of the ratio value to the peak-to-peak BECI value, defining a variable as a maximum of the ratio value and the peak-to-peak value scaled accordingly, and comparing the variable to one or more threshold values to determine a contact status.

The step of determining contact status based on a combination of the baseline BECI value, the measured BECI value, and the peak-to-peak value may further include applying the formula:

$$D = \max\left(\frac{M}{M_B}, S_V * \min(PP, PP_C)\right),$$

where D is a contact variable, M is the measured BECI value, $M_B$ is the baseline BECI value, PP is the peak-to-peak value calculated during the given interval, $PP_C$ is a ceiling or maximum peak-to-peak BECI measurement, and $S_V$ is a scaling variable selected to properly scale the peak-to-peak BECI measurements to a reference frame of a ratio defined by $M/M_B$.

The contact variable may be compared to one or more threshold values to determine the contact status, wherein if the contact variable is less than a first threshold then a 'no contact' status is assigned, greater than a first threshold and less than a second threshold an 'intermittent contact' status is assigned, and greater than the second threshold a 'good contact' status is assigned.

The invention claimed is:

1. A method of determining contact status of electrodes, the method comprising:
   applying drive signals between pairs of electrodes;
   measuring a bipolar electrode complex impedance (BECI) value generated in response to the drive signals over a collection period;
   determining a baseline BECI value representing a minimum value measured during the collection period; and
   determining contact status by:
      applying drive signals between pairs of electrodes over a given interval;
      measuring a BECI value generated in response to the drive signals;
      measuring a peak-to-peak value associated with the BECI values measured over the given interval; and
      determining contact status based on a combination of the baseline BECI value, the measured BECI value, and the peak-to-peak value associated with the measured BECI values.

2. The method of claim 1, wherein the BECI value includes a real component and a quadrature component, wherein the baseline BECI value, the measured BECI value, and the peak-to-peak value all represent magnitudes of the BECI value.

3. The method of claim 1, wherein determining a baseline BECI value representing a minimum value measured during the collection period includes applying a filter to the measured BECI values to filter erroneous minimum values resulting from contact with other electrodes.

4. The method of claim 1, wherein measuring a peak-to-peak value associated with the measured BECI values over the given interval includes:
   calculating a largest positive deflection in BECI values measured over the given interval.

5. The method of claim 1, wherein determining contact status based on a combination of the baseline BECI value, measured BECI value, and peak-to-peak value further includes:
   calculating a ratio value that represents the ratio of the measured BECI value to the baseline BECI value;
   scaling at least one of the ratio value or the peak-to-peak value to allow comparison of the ratio value to the peak-to-peak value;
   defining a variable as a maximum of the ratio value and the peak-to-peak value scaled accordingly; and
   comparing the variable to one or more threshold values to determine a contact status.

6. The method of claim 1, wherein determining contact status based on a combination of the baseline BECI value, the measured BECI value, and the peak-to-peak value further includes applying an equation:

$$D = \max\left(\frac{M}{M_B}, S_V * \min(PP, PP_C)\right),$$

where D is a contact variable, M is the measured BECI value, $M_B$ is the baseline BECI value, PP is the peak-to-peak value calculated during the given interval, $PP_C$ is a ceiling or maximum peak-to-peak BECI measurement, and $S_V$ is a scaling variable selected to properly scale the peak-to-peak BECI measurements to a reference frame of a ratio defined by $M/M_B$.

7. The method of claim 6, wherein the contact variable is compared to one or more threshold values to determine the contact status, wherein if the contact variable is less than a first threshold then a 'no contact' status is assigned, greater than a first threshold and less than a second threshold an 'intermittent contact' status is assigned, and greater than the second threshold a 'good contact' status is assigned.

8. A system for use with a medical device configured for insertion within a patient, comprising:
   a signal generator configured to apply a drive signal to one or more pairs of electrodes located on the medical device;
   a measurement circuit configured to measure responses of the electrode pairs to the drive signal;
   a contact assessment module configured to generate bipolar electrode complex impedance (BECI) values for each of the electrode pairs, determine a baseline BECI value representing a minimum BECI value measured during a collection period, measure, subsequently measure a BECI value generated in response to the applied drive signals over a given interval, measure a peak-to-peak value associated with the measured BECI values over the given interval, and determine a contact status based on a combination of the baseline BECI value, the measured BECI value, and the peak-to-peak value associated with the measured BECI values; and
   a display for displaying proximities of the electrodes relative to the tissue based on outputs received from the contact assessment module.

9. The system of claim 8, wherein the contact assessment module determines a baseline BECI value representing a minimum value measured during the collection period by applying a filter to the measured BECI values to filter erroneous minimum values resulting from contact with other electrodes.

10. The system of claim 8, wherein the contact assessment module measures a peak-to-peak value by calculating a largest positive deflection in BECI values measured over the given interval.

11. The system of claim 8, wherein the contact assessment module determines contact status based on a combination of the baseline BECI value, measured BECI value, and peak-to-peak value by calculating a ratio value that represents the ratio of the measured BECI value to the baseline BECI value, scaling at least one of the ratio value or the peak-to-peak BECI value to allow comparison of the ratio value to the peak-to-peak BECI value, defining a variable as a maximum of the ratio value and the peak-to-peak value scaled accordingly, and comparing the variable to one or more threshold values to determine a contact status.

12. The system of claim 8, wherein the contact assessment module determines contact status based on the formula:

$$D = \max\left(\frac{M}{M_B}, S_V * \min(PP, PP_C)\right),$$

where D is a contact variable, M is the measured BECI value, $M_B$ is the baseline BECI value, PP is the peak-to-peak value calculated during the given interval, $PP_C$ is a ceiling or maximum peak-to-peak BECI measurement, and $S_V$ is a scaling variable selected to properly scale the peak-tip-peak BECI measurements to a reference frame of a ratio defined by $M/M_B$.

13. The system of claim 12, wherein the contact assessment module compares the contact variable D to one or more threshold values to determine the contact status, wherein if the contact variable is less than a first threshold then a 'no contact' status is assigned, greater than a first threshold and less than a second threshold an 'intermittent contact' status is assigned, and greater than the second threshold a 'good contact' status is assigned.

14. A contact assessment system for determining a contact state of an electrode included as part of an electrode pair located at a distal end of a medical instrument, the system comprising:
  input configured to receive signals collected in response to a source signal applied across the electrode pair; and
  a processor configured to, upon execution of specific program instructions stored on a computer-readable storage medium:
    calculate a bipolar electrode complex impedance (BECI) values based on the received input signals during a collection period;
    determine a baseline BECI value representing a minimum value measured during the collection period; and
    determine a contact status by subsequently applying drive signals between the electrode pair over a given interval, measuring a BECI value generated in response to the applied drive signals over the given interval, measuring a peak-to-peak value associated with the measured BECI values over the given interval, and utilizing a combination of the baseline BECI value, the measured BECI value, and the peak-to-peak value associated with the measured BECI values to determine the contact status of the electrode.

15. The system of claim 14, wherein the processor outputs the determined contact status to a display.

16. The system of claim 14, wherein the step of determining a baseline BECI value representing a minimum value measured during the collection period further includes applying a filter to the measured BECI values to filter erroneous minimum values resulting from contact with other electrodes.

17. The system of claim 14, wherein the step of measuring a peak-to-peak BECI value associated with the measured BECI values over the given interval further includes calculating a largest positive deflection in BECI values measured over the given interval.

18. The system of claim 14, wherein the step of determining contact status based on a combination of the baseline BECI value, measured BECI value, and peak-to-peak value further includes:
  calculating a ratio value that represents the ratio of the measured BECI value to the baseline BECI value;
  scaling at least one of the ratio value or the peak-to-peak BECI value to allow comparison of the ratio value to the peak-to-peak BECI value;
  defining a variable as a maximum of the ratio value and the peak-to-peak value scaled accordingly; and
  comparing the variable to one or more threshold values to determine a contact status.

19. The system of claim 14, wherein the step of determining contact status based on a combination of the baseline BECI value, the measured BECI value, and the peak-to-peak value further includes applying the formula:

$$D = \max\left(\frac{M}{M_B}, S_V * \min(PP, PP_C)\right),$$

where D is a contact variable, M is the measured BECI value, $M_B$ is the baseline BECI value, PP is the peak-to-peak value calculated during the given interval, $PP_C$ is a ceiling or maximum peak-to-peak BECI measurement, and $S_V$ is a scaling variable selected to properly scale the peak-to-peak BECI measurements to a reference frame of a ratio defined by $M/M_B$.

20. The system of claim 19, wherein the contact variable is compared to one or more threshold values to determine the contact status, wherein if the contact variable is less than a first threshold then a 'no contact' status is assigned, greater than a first threshold and less than a second threshold an 'intermittent contact' status is assigned, and greater than the second threshold a 'good contact' status is assigned.

* * * * *

UNITED STATES PATENT AND TRADEMARK OFFICE
CERTIFICATE OF CORRECTION

| | | |
|---|---|---|
| PATENT NO. | : 11,950,833 B1 | Page 1 of 1 |
| APPLICATION NO. | : 18/096188 | |
| DATED | : April 9, 2024 | |
| INVENTOR(S) | : Eric J. Voth and Jeffrey A. Schweitzer | |

It is certified that error appears in the above-identified patent and that said Letters Patent is hereby corrected as shown below:

In the Claims

Column 16, Line 50, Claim 8 "during a collection period, measure, subsequently measure" should read --during a collection period, subsequently measure--

Signed and Sealed this
Thirty-first Day of December, 2024

Derrick Brent
*Acting Director of the United States Patent and Trademark Office*